(12) United States Patent
Papanyan (10) Patent No.: US 6,388,251 B1
(45) Date of Patent: May 14, 2002

(54) OPTICAL PROBE FOR ANALYSIS OF FORMATION FLUIDS

(75) Inventor: Valeri Papanyan, Houston, TX (US)

(73) Assignee: Baker Hughes, Inc., Houston, TX (US)

( * ) Notice: Subject to any disclaimer, the term of this patent is extended or adjusted under 35 U.S.C. 154(b) by 0 days.

(21) Appl. No.: 09/228,721

(22) Filed: Jan. 12, 1999

(51) Int. Cl.⁷ .............................................. G01V 8/00
(52) U.S. Cl. ............... 250/269.1; 250/256; 250/339.11; 250/341.8
(58) Field of Search ..................... 250/256, 269.1, 250/339.11, 341.8

(56) References Cited

U.S. PATENT DOCUMENTS

| | | | | |
|---|---|---|---|---|
| 2,334,475 A | * | 11/1943 | Claudet ...................... 250/268 |
| 3,859,851 A | | 1/1975 | Urbanosky ............... 73/152.24 |
| 4,473,295 A | * | 9/1984 | Doyle ......................... 356/244 |
| 4,490,845 A | * | 12/1984 | Steinbruegge et al. ...... 356/300 |
| 4,994,671 A | | 2/1991 | Safinya et al. .............. 250/255 |
| 5,051,551 A | | 9/1991 | Doyle ....................... 250/341.2 |
| 5,167,149 A | | 12/1992 | Mullins et al. ............... 73/155 |
| 5,266,800 A | | 11/1993 | Mullins ....................... 250/256 |
| 5,306,909 A | * | 4/1994 | Jones et al. .................. 250/255 |
| 5,310,260 A | * | 5/1994 | Schnietinger et al. ....... 374/142 |
| 5,553,680 A | * | 9/1996 | Hathaway ..................... 175/78 |
| 5,663,559 A | * | 9/1997 | Auzerais et al. ......... 250/269.1 |
| 5,831,743 A | | 11/1998 | Ramos et al. ............... 356/445 |
| 5,956,132 A | | 9/1999 | Donzier ...................... 356/133 |

FOREIGN PATENT DOCUMENTS

EP 0 747 569 A2 12/1996
WO WO 9900575 A 1/1999

* cited by examiner

*Primary Examiner*—Constantine Hannaher
*Assistant Examiner*—Shun Lee
(74) *Attorney, Agent, or Firm*—Madan, Mossman & Sriram, PC (57) ABSTRACT

A formation fluid analysis tool has an optical probe that is inserted into the formation. The optical probe carries an internal reflectance crystal and is inserted into the formation so as to get past the mud cake, the flushed zone and the invaded zone and thus be in contact with virgin formation fluid. An acousto-optical tunable filter (AOTF) transmits a single wavelength of light from a broad band light source, the wavelength being controlled by a microwave signal from a processor. This monochromatic light is carried by an optic fiber to the internal reflectance crystal where it undergoes total reflection at the crystal faces in contact with the formation fluid. An evanescent wave propagates into the fluid with a depth of penetration related to the absorption of the light in the fluid. The reflected light carries information about this absorption which is determined by the chemical composition of the fluid. A return fiber conveys the reflected light back to a spectrometer. A processor determines the absorption at the wavelength of the monochromatic light by comparing the energy in the reflected light to the energy in the incident light. By repeating this process at a number of different wavelengths, the absorption spectrum of the fluid is determined. Principal component analysis or least squares analysis of this absorption spectrum using known absorption spectra of constituents likely to occur in the fluid gives the composition of the fluid in terms of these constituents.

23 Claims, 5 Drawing Sheets

OPTICAL PROBE FOR ANALYSIS OF FORMATION FLUIDS

BACKGROUND OF THE INVENTION

1. Field of the Invention

This invention relates generally to apparatus and methods for analyzing the chemical composition of formation fluids, and more particularly, to apparatus and method for using infrared spectral analysis to determine the quantities of methane, water and various types of oils in a formation fluid.

2. Description of the Related Art

In the oil and gas industry, formation testing tools have been used for monitoring formation pressures along a wellbore, obtaining formation fluid samples from the wellbore and predicting performance of reservoirs around the wellbore. Such formation testing tools typically contain an elongated body having an elastomeric packer that is sealingly urged against the zone of interest in the wellbore to collect formation fluid samples in storage chambers placed in the tool.

During drilling of a wellbore, a drilling fluid ("mud") is used to facilitate the drilling process and to maintain a pressure in the wellbore greater than the fluid pressure in the formations surrounding the wellbore. This is particularly important when drilling into formations where the pressure is abnormally high: if the fluid pressure in the borehole drops below the formation pressure, there is a risk of blowout of the well. As a result of this pressure difference, the drilling fluid penetrates into or invades the formations for varying radial depths (referred to generally as invaded zones) depending upon the types of formation and drilling fluid used. The formation testing tools retrieve formation fluids from the desired formations or zones of interest, test the retrieved fluids to ensure that the retrieved fluid is substantially free of mud filtrates, and collect such fluids in one or more chambers associated with the tool. The collected fluids are brought to the surface and analyzed to determine properties of such fluids and to determine the condition of the zones or formations from where such fluids have been collected.

One feature that all such testers have in common is a fluid sampling probe. This may consist of a durable rubber pad that is mechanically pressed against the rock formation adjacent the borehole, the pad being pressed hard enough to form a hydraulic seal. Through the pad is extended one end of a metal tube that also makes contact with the formation. This tube ("probe") is connected to a sample chamber that, in turn, is connected to a pump that operates to lower the pressure at the attached probe. When the pressure in the probe is lowered below the pressure of the formation fluids, the formation fluids are drawn through the probe into the well bore to flush the invaded fluids prior to sampling. In some prior art devices, a fluid identification sensor determines when the fluid from the probe consists substantially of formation fluids; then a system of valves, tubes, sample chambers, and pumps makes it possible to recover one or more fluid samples that can be retrieved and analyzed when the sampling device is recovered from the borehole.

It is critical that only uncontaminated fluids are collected, in the same condition in which they exist in the formations. Commonly, the retrieved fluids are found to be contaminated by drilling fluids. This may happen as a result of a poor seal between the sampling pad and the borehole wall, allowing borehole fluid to seep into the probe. The mudcake formed by the drilling fluids may allow some mud filtrate to continue to invade and seep around the pad. Even when there is an effective seal, borehole fluid (or some components of the borehole fluid) may "invade" the formation, particularly if it is a porous formation, and be drawn into the sampling probe along with connate formation fluids.

U.S. Pat. No. 4,994,671 issued to Safinya et al. discloses a device in which visible and near infrared (IR) analysis of the fluids is done in the borehole, without having to transport recovered samples of the fluid to the surface for chemical analysis. The IR part of the electromagnetic spectrum (0.8 to 25 $\mu$m wavelength region, or equivalently wavenumbers of 12500 to 400 cm$^{-1}$) of a substance contains absorption features due to the molecular vibrations of the constituent molecules. The absorptions arise from both fundamentals (single quantum transitions occurring in the mid-infrared region from 2.5–25.0 $\mu$m) and combination bands and overtones (multiple quanta transitions occurring in the mid- and the near-infrared region from 0.8–2.5 $\mu$m). The position (frequency or wavelength) of these absorptions contain information as to the types of molecular structures that are present in the material, and the intensity of the absorptions contains information about the amounts of the molecular types that are present. To use the information in the spectra for the purpose of identifying and quantifying either components or properties requires that a calibration be performed to establish the relationship between the absorbances and the component or property that is to be estimated. For complex mixtures, where considerable overlap between the absorptions of individual constituents occurs, such calibrations must be accomplished using various chemometric data analysis methods.

In complex mixtures, each constituent generally gives rise to multiple absorption features corresponding to different vibrational motions. The intensities of these absorptions will all vary together in a linear fashion as the concentration of the constituent varies. Such features are said to have intensities which are correlated in the frequency (or wavelength) domain. This correlation allows these absorptions to be mathematically distinguished from random spectral measurement noise which shows no such correlation. The linear algebra computations which separate the correlated absorbance signals from the spectral noise form the basis for techniques such as Principal Components Regression (PCR) and Partial Least Squares (PLS). As is well known, PCR is essentially the analytical mathematical procedure of Principal Components Analysis (PCA), followed by regression analysis.

PCR and PLS have been used to estimate elemental and chemical compositions and to a lesser extent physical or thermodynamic properties of solids and liquids based on their mid- or near-infrared spectra. These chemometric methods involve: [1] the collection of mid- or near-infrared spectra of a set of representative samples; [2] mathematical treatment of the spectral data to extract the Principal Components or latent variables (e.g. the correlated absorbance signals described above); and [3] regression of these spectral variables against composition and/or property data to build a multivariate model. The analysis of new samples then involves the collection of their spectra, the decomposition of the spectra in terms of the spectral variables, and the application of the regression equation to calculate the composition/properties.

In Safinya et al. light the visible and near IR region is passed through the fluid sample. A spectrometer measures the spectrum of the transmitted and the back scattered light, and knowing the spectrum of the incident light, transmission and backscattered absorption spectra for the sample are determined. Using absorption spectra of water, gas, crude and refined oils, and drilling fluids, a least squares analysis is performed that models the observed spectra as a weighted sum of the spectra of its components, the least squares analysis giving the composition of the fluid in terms of weights of the various components.

Safinya et al. use only the visible and near IR regions that contain only harmonics and combinations of molecular vibrations. The harmonic and combination absorption bands are much weaker than the fundamental absorption bands, and, for this reason, transmission methods of sampling are used to detect absorption spectra. The path lengths through the sample that are necessary to get detectable measurements are large, being typically 5 mm. or more. Even at this length of transmission, signal levels are lower and the spectral analysis of the harmonics and combinations is complicate. Also of importance is the fact that in downhole applications, the presence of particulate matter, microscopic particles or bubbles leads to scattering. This scattering drastically increases the optical density and reduces the ability to detect spectral features of the sample. This effect is discussed below with reference to FIGS. 1 and 2.

As noted above, the fundamental absorbances corresponding to the functional groups of organic chemicals fall in the mid infrared region. The absorbances are generally strong and to use transmission methods on such fluids would require transmission paths of 25 $\mu$m or less. With spacings of this magnitude it is difficult to get good fluid flow through the optical cell. In addition, there are noticeable interference fringes. The method and apparatus of this invention helps overcome this problem.

Diffuse and specular reflectance methods have been used in prior art applications of near infrared analysis. Diffuse reflectance measurements require a large solid angle of data collection with a relatively large illuminated area to average out sample inhomogeneities. Consequently, diffuse reflectance is not suitable for measurement of small samples at low flow rates that are characteristic of reservoir fluid monitoring.

Specular reflectance is used in U.S. Pat. No. 5,167,149 issued to Mullins et al. Disclosed therein is an invention for analyzing the composition of multiphasic formation fluids, and specifically for detecting the presence of gas in a flow stream that comprises oil, water, gas or particulates within the borehole. The apparatus comprises a flow line for containing the fluid and a light source for transmitting light towards the fluid in the flow line. A prism transmits light from the source to the fluid and forms an interface with the flow line. The interface reflects the light from the source and a detector array detects the light. The angle of incidence at which total reflection of the light takes place provides a measure of the refractive index of the fluid in contact with the prism surface. As the refractive index of gas and liquids are essentially different, the amount of gas in the fluid can be measured. Specular reflectance methods are effective in identifying the composition of a multiphasic fluid in terms of its constituent phases but are not particularly useful for identifying the chemical composition of a single phase. However, due to the fact that at sufficiently high pressures, the refractive index of the gas phase approaches the refractive index of liquid hydrocarbons, specular reflectance methods cannot be used to determine methane concentration at high pressures.

U.S. patent application Ser. No. 09/111,368 which is assigned to the owner of the present invention discloses the use of attenuated total reflectance (ATR) methods for analysis of the absorbances at fundamental frequencies for the analysis of borehole fluids, particularly methane, in a flow detector. ATR methods make use of the fact that when light is incident at an interface between a first medium of a higher refractive index and a second medium of lower refractive index, there exists a critical angle beyond which total reflectance of the light takes place within the first medium. However, even beyond the critical angle, an evanescent wave is propagated into the second medium with a characteristic depth of penetration $d_p$ into the second medium given by $$d_p = \frac{\lambda}{2\pi n_{21} \sqrt{\sin^2\theta - n_{21}^2}}$$

where $n_{21} = n_2/n_1$, the ratio of the refractive indices of the second and first media and $\lambda$ is the wavelength of the radiation in vacuum and the angle $\theta$ exceeds the critical angle.

The energy carried by this evanescent wave manifests itself as a decrease in the energy of the reflected wave, a measurable quantity. ATR methods thus effectively function like the equivalent of a transmission cell having a transmission length $d_e$ given by $d_e = 0.5 (d_s + d_p)$ where $$d_s = \frac{n_{21}\lambda\cos\theta}{\pi n_1 (1 - n_{21}^2)\sqrt{\sin^2\theta - n_{21}^2}}$$

is the effective thickness for light polarized perpendicular to the plane of incidence and $$d_p = \frac{n_{21}\lambda\cos\theta}{\pi n_1 (1 - n_{21}^2)\sqrt{\sin^2\theta - n_{21}^2}\,[(1 + n_{21}^2)\sin^2\theta - n_{21}^2]}$$

is the effective thickness for light polarized in the plane of incidence. Some calculations will show that the effective thickness is of the order of the wavelength of the light.

Figure 1:
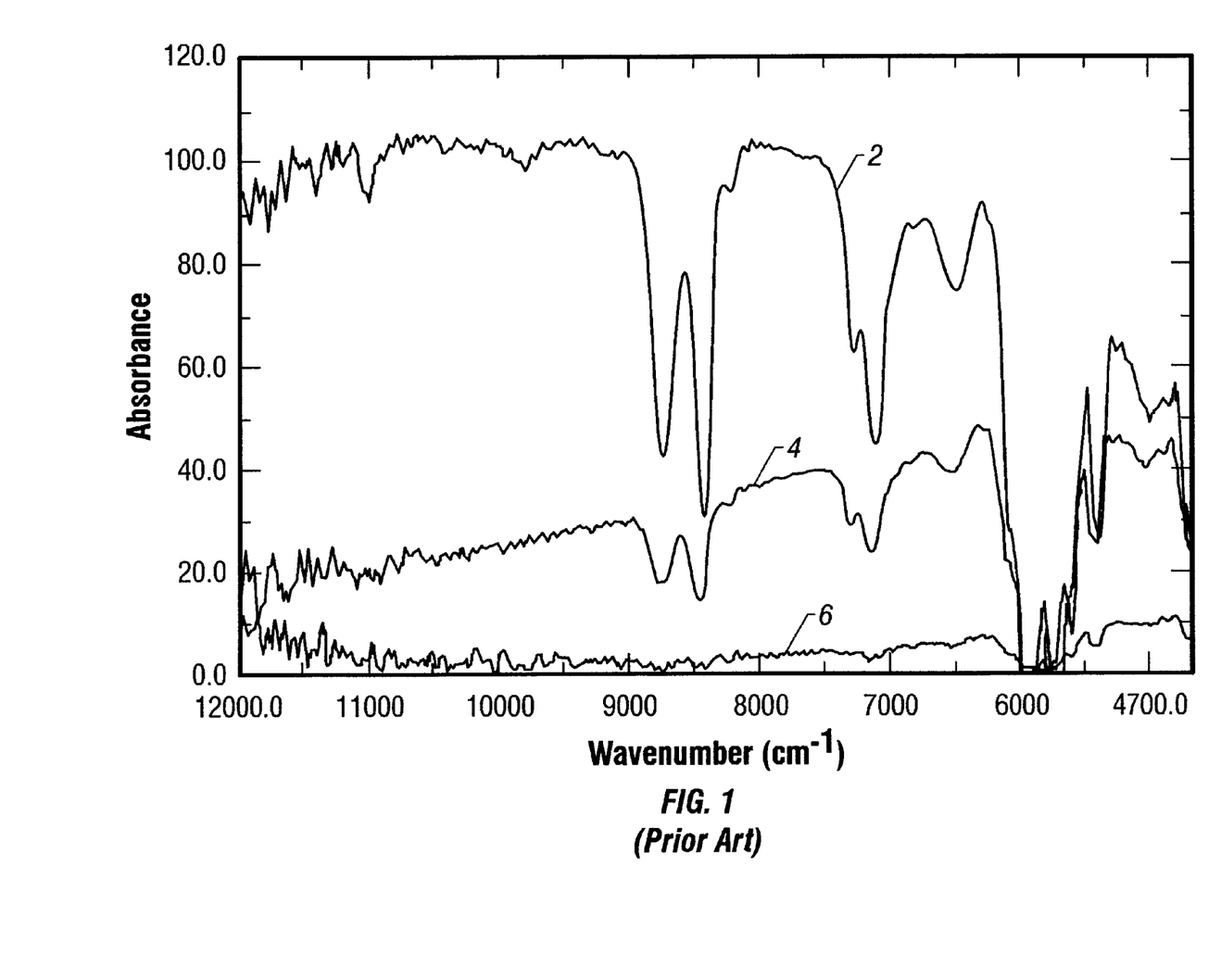
FIG. 1 (PRIOR ART) shows the effect of addition of a small amount of a light absorbing material ($TiO_2$) on the absorbance of silicone oil as de termined by transmission techniques.
Figure 2:
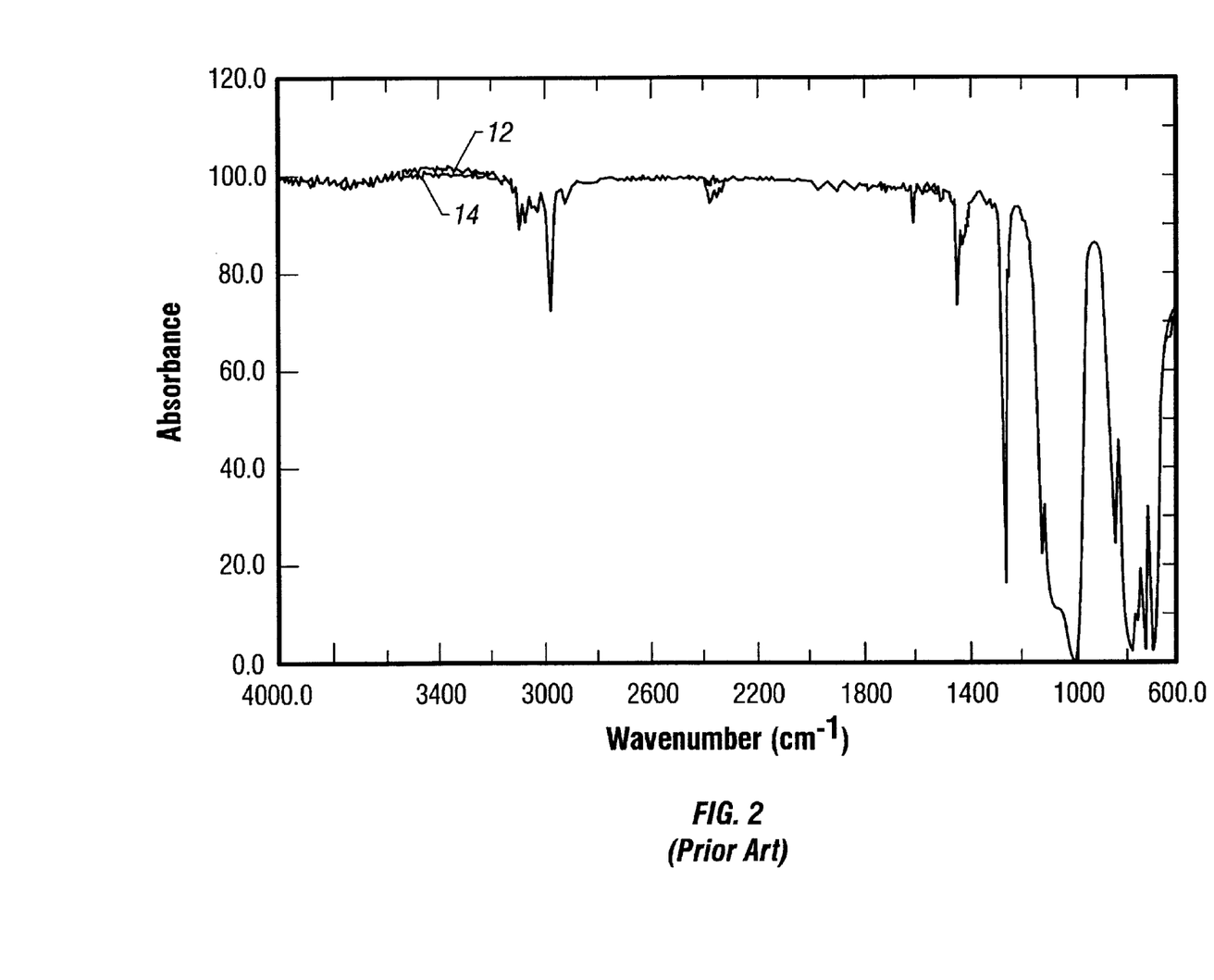
FIG. 2 (PRIOR ART) shows the effect of the addition of $TiO_2$ on the absorbance of silicone oil as determined by attenuated total reflectance (ATR) techniques.

Unlike transmission techniques, ATR methods are relatively insensitive to the presence of small particles in the fluid. This advantage of ATR methods is brought out by comparing FIGS. 1 and 2 (Prior art). In both figures, the abscissa is the wavenumber and the ordinate is the absorption. In FIG. 1, the near infrared transmission spectrum of pure silicone oil 2 may be compared with that of silicone oil with 0.015% of $TiO_2$ 4 and of silicone oil with 0.125% of $TiO_2$ 6. As can be seen, the addition of even a small amount of an absorbing material like $TiO_2$ makes greatly increases the absorption of light and makes it almost impossible to pick out the underlying "signal". In comparison, using ATR techniques, as shown in FIG. 2, the mid infrared absorbance spectrum of pure silicone oil 12 is not significantly affected by the addition of $TiO_2$ 14 in quantities as large as 0.5%, much larger than the values used in FIG. 1.

All of the above methods also suffer from the drawback that the fluid sample being evaluated is in the borehole inside the measurement apparatus and the fluid sample recovered from the formation may be contaminated by borehole fluids even with the most careful of sampling techniques. Any analysis technique must therefore account for the presence of the drilling fluid and its absorbance spectrum. There is a need for an invention that accurately and speedily provides a measurement of the composition of formation fluids without contamination by drilling fluids and particulate matter. The present invention satisfies this need.

SUMMARY OF THE INVENTION

The present invention provides an apparatus and a method for determination of the composition of a formation fluid. An optical probe carrying a sapphire crystal is inserted into the formation so as to get past the mud cake, the flushed zone and the invaded zone and thus he in contact with virgin formation fluid. An acousto-optical tunable filter transmits a single wavelength of light from a broad band light source. This monochromatic light is carried by an optic fiber to the internal reflectance sapphire crystal where it undergoes total reflection at the crystal faces in contact with the formation fluid. An evanescent wave propagates into the fluid with a depth of penetration related to the absorption of the light in the fluid. The reflected light carries information about this absorption. A return fiber conveys the reflected light back to a spectrometer. A processor determines the absorption at the wavelength of the monochromatic light by comparing the energy in the reflected light to the energy in the incident light. By repeating this process at a number of different wavelengths, the absorption spectrum of the fluid is determined. Principal component analysis of this absorption spectrum using known absorption spectra of chemicals likely to occur in the fluid gives the composition of the fluid in terms of these chemicals.

BRIEF DESCRIPTION OF THE DRAWINGS

For detailed understanding of the present invention, references should be made to the following detailed description of the preferred embodiment, taken in conjunction with the accompanying drawings, in which like elements have been given like numerals and wherein.

DESCRIPTION OF THE PREFERRED EMBODIMENT

Figure 3:
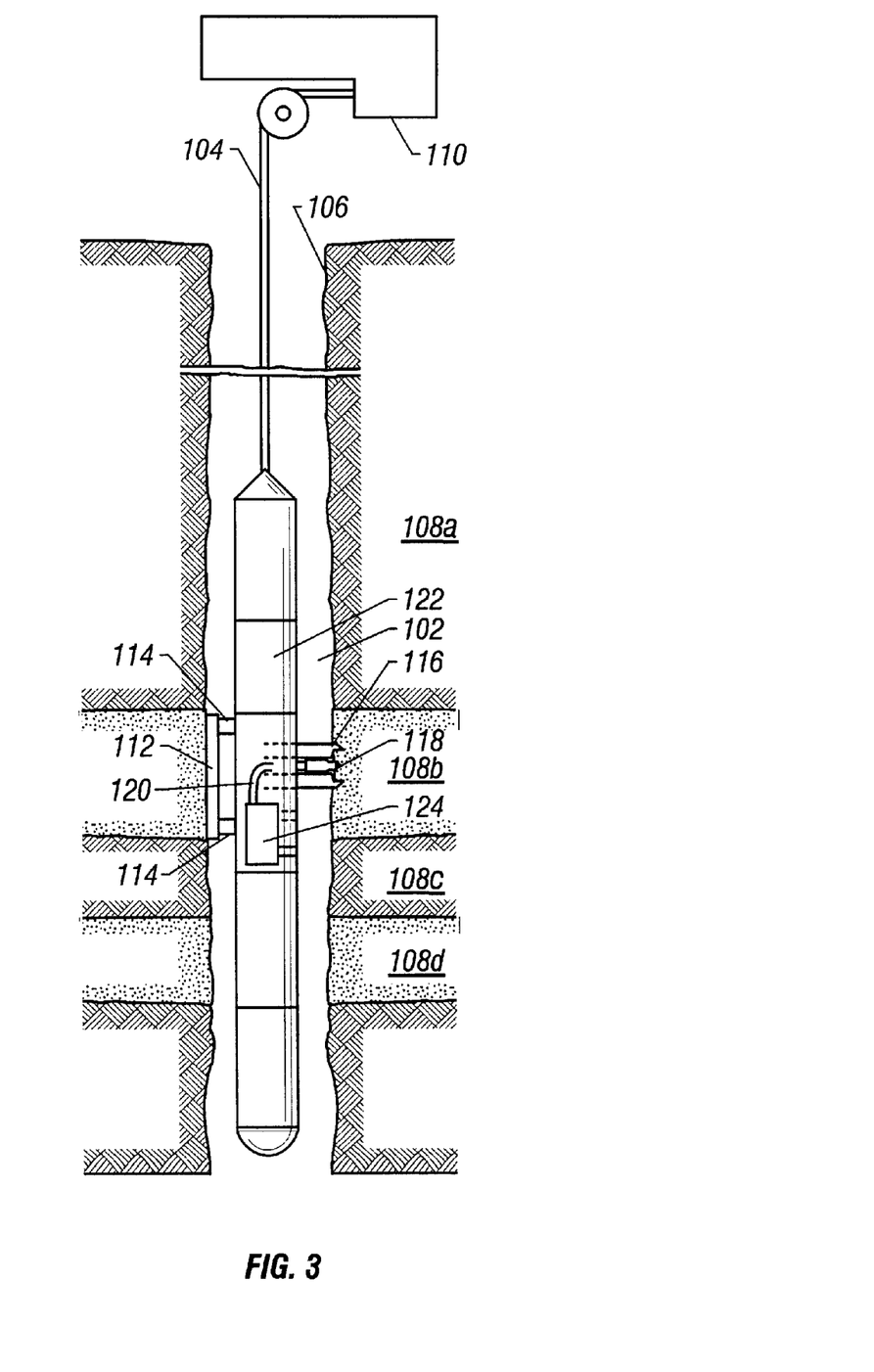
FIG. 3 is a simplified schematic illustration of an embodiment of the present invention

FIG. 3 shows the schematic arrangement of an embodiment of the present invention. A borehole logging tool 102 is suspended by a wireline 104 inside a borehole 106 drilled into formations 108a, 108b, 108c, 108d etc. The wireline is a typical multiconductor cable, the other end of which is spooled in the usual fashion on a winch (not shown) with the conductors connected to a surface processing and control unit 110. The tool has an elongated body that includes a downhole processor 122. The body of the tool is provided with an anchoring mechanism for anchoring the tool to the borehole wall. In the embodiment shown, the anchoring is accomplished by means of pistons 114 that push a pad 112 against the walls of the borehole.

The tool is provided with a drill bit 116 carried on a drilling tube (not shown in FIG. 3) for drilling a hole into borehole wall. The drill bit is in the shape of a core bit for drilling out a small corehole into the borehole wall. The tool is provided with a telescopic probe 118 adapted to follow the drill bit into the formation and make contact with the formation fluid. Details of the probe/drill assembly are discussed below with reference to FIG. 4. Not shown is a sealing pad that is used to prevent flow of borehole drilling fluid into the corehole.

A pair of optical fibers 120 lead from the probe into an optical assembly 124, details of which are discussed below with reference to FIG. 5.

Figure 4:
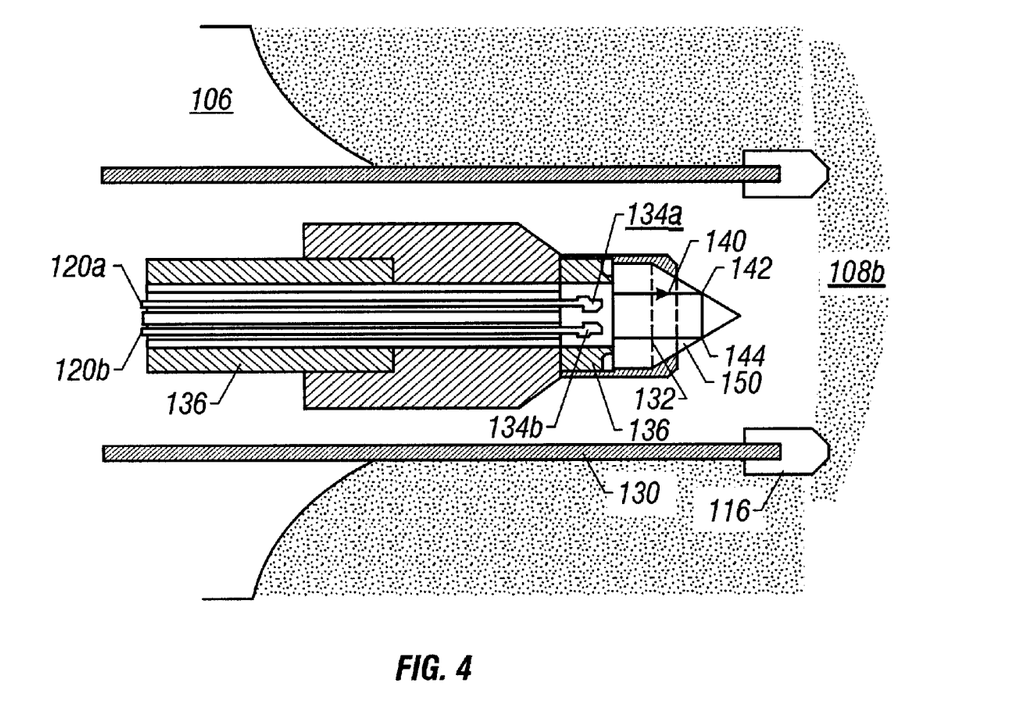
FIG. 4 is a schematic illustration of the optical probe of the present invention.

Turning now to FIG. 4, the drill bit 116 and drilling tube 130 are shown after having drilled a corehole into the formation 108b through the borehole wall. The pad for preventing the flow of borehole fluids into the corehole is not shown. The optical probe includes a sapphire crystal 132 at its tip connected by means of optical connects 134a to the incoming optical fiber 120a and the connector 134b to the return optical fiber 120b. Once the corehole has been drilled into the formation, the telescopic cylinder 136 is extended so that the internal reflectance crystal 132 contacts the formation and the fluid therein.

When light is conveyed into the crystal by means of the optical fiber 120a, within the crystal it follows a ray path as indicated by the ray 140, undergoes multiple reflections at points indicated by 142 and 144 and returns through connector 134b to the return fiber 120b.

The internal reflectance crystal must have a high refractive index in the IR region, be chemically resistant and mechanically strong. Sapphire is used in a preferred embodiment of the invention. Sapphire has a refractive index of 1.74. The tapered surface 150 of the crystal is angled at 30° so that the ray 140 exceeds the critical angle of 60° at the surface of the crystal with respect to formation fluids that may have refractive indices up to 1.5, and undergoes total reflection. Sapphire is also transparent in the near and mid IR region, chemically resistant, mechanically hard and relatively inexpensive. This makes it the most cost-effective for downhole applications. Cubic zirconia that has characteristics comparable to those of sapphire may also be used. In yet another embodiment of the invention, the ATR element may be made of diamond. Diamonds are more expensive than sapphires or cubic zirconia, but have the advantage of a higher refractive index, transparency and extreme hardness. By using diamond as the material for the ATR, the crystal can be as small is 4 to 8 mm. in diameter and −2 mm in thickness.

As would be known to those versed in the art, the electric field amplitude of the light falls off exponentially with distance from the sapphire-fluid interface within the formation fluid, a typical depth of penetration for this evanescent wave in the fluid being of the order of the wavelength of the incident light. This evanescent wave is attenuated by the absorption properties of the formation fluid. Conservation of energy must hold, so that the reflected wave within the crystal 132 has an imprint of this absorption. Thus, by making measurements of the amplitude of the incident light beam in fiber 120a and of the reflected light beam in the fiber 120b, the amount of light absorbed by the fluid at the frequency of the incident light may be determined.

Figure 5:
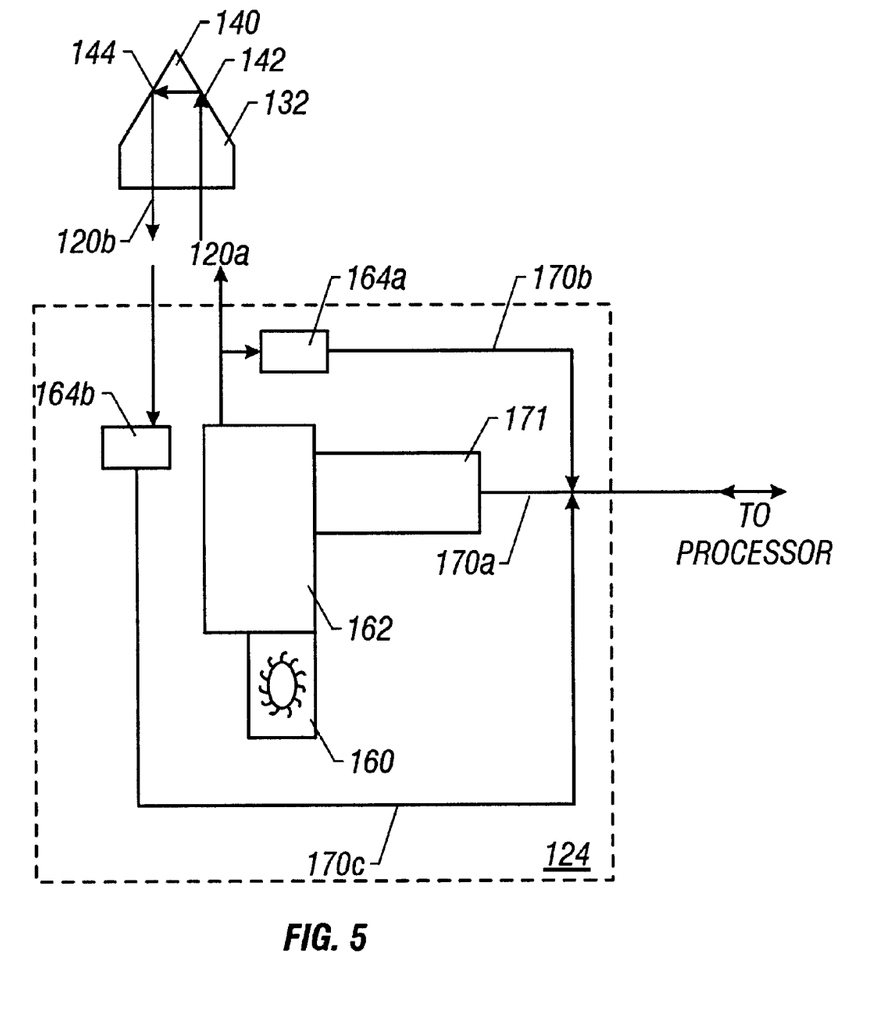
FIG. 5 illustrates the optical generator-detector arrangement used in the present invention.

Turning now to FIG. 5, the optical assembly 124 includes a broad band light source 160. In a preferred embodiment of the invention, the broad band light source is an incandescent lamp. The light from this broad band light source 160 is passed to an acousto-optical tunable filter (AOTF) 162 that transmits light of a single frequency (or equivalently, having a single wavelength) to the optic fiber 120a, the value of the single frequency being determined by a microwave frequency applied to the AOTF 162 provided by a radio frequency (RF) generator 171. This RF generator 171 is controlled by the processor 122 (see FIG. 3) via leads 170a, thus controlling the wavelength of the incident light in the optic fiber 120a. The energy of the monochromatic light in the optic fiber 120a is measured by a reference detector 164a and this measurement is sent by leads 170b to the processor 122. The light returning from the optical probe via the optic fiber 120b is passed to the main detector 164b and a signal indicative of the strength of this returning light is sent to the processor by leads 170c.

The operation of the tool may now be understood with reference to FIGS. 3–5. The tool is positioned on the wireline at a depth at which measurements are to be made. This may be done either by the surface processor 110 or the downhole processor 122. Under the control of one of the two processors, the clamping mechanism 114 and the drill bit 116 are activated, with the drill bit carving out a hole in the formation. The optical probe 118 is inserted into the hole carved out by the drill bit. Those versed in the art would recognize that in order to obtain a proper measurement of the properties of the formation fluid, the drill bit 116 and the end of the probe 118 must penetrate into the borehole wall through the mudcake and the invaded zone and into a region where the formation fluid is uncontaminated by drilling fluids. The flow of borehole fluids into the formation may be reduced by use of the sealing pad discussed but not shown above. In addition, in wireline logging applications, a pump at the surface may be used to maintain the borehole in a slightly underpressured state to avoid contamination of the formation with borehole fluids. In an alternate embodiment of the invention, the formation tester tool is provided with a pump in fluid communication with the corehole to maintain a fluid flow out of the formation, thus reducing the risk of contamination of the formation fluid with borehole fluids. Such methods of avoiding contamination of formation fluids by borehole fluids would be known to those versed in the art.

The processor 122 is programmed to scan a predefined spectral interval or to obtain data at a number of selected frequencies. For each of the sampled frequencies, the processor 122 directs the RF generator 171 to send a corresponding microwave signal to the AOTF 162 by via the lead 170a. The broad-band light source 160 produces light that covers the entire IR spectral interval, out of which the AOTF 162 filters light at the selected frequency through optic fiber 120a to the probe. At the same time, the processor 122 receives a signal indicative of the energy in the light at the selected frequency via lead 170b. The light at the selected frequency is passed into the sapphire crystal by the optical connector 134a. This light undergoes total reflection at the face of the crystal that is in contact with the formation fluid. The reflected light passes through the optical connector 134b to the optic fiber 120b and thence to the detector 164b. The detector sends a signal to the processor 122 via lead 170c that is indicative of the energy in the reflected light.

The apparatus is calibrated to account for energy losses in the optic fibers 120a, 120b. This is done by methods that would be familiar to those versed in the art. After compensating for the losses in the optic fibers, the ratio of the energy at 170c to the energy at 170b is indicative of the absorption of the fluid at the selected frequency. From these measurements, a value of the absorption at the selected frequency is obtained. This process is repeated at a number of different values of the selected frequency to give an absorption spectrum for the fluid. As the AOTF operates at frequencies in the range of 10 to 80 MHZ, one scan through the operating wavelength range takes less than one millisecond, so that more than 100 scans can be performed in less than 1 second, and subsequently averaged and preprocessed by the downhole processor.

The optical probe 118 is withdrawn from the formation and the drill bit 116 is retracted. The clamping mechanism 114 is retracted and the tool is moved to another position in the borehole at which chemical analysis of the formation fluid is to be performed, and the process described above is repeated.

The analysis of the data obtained by the apparatus may be carried out by prior art methods to give a chemical analysis of the formation fluid. One such prior art method models the observed absorbance spectrum as a weighted sum of a number of components, each having a known absorbance spectrum. The determination of the composition is then a mathematical problem in least squares optimization to determine the weights associated with the components. As long as the number of frequencies at which the absorbance is measured is greater than the number of weights, the equations are overdetermined and a solution may be readily found. Further variations of the method involve the selection of frequencies at which measurements are made: this has the benefit of reducing the time spent in making measurements. Principal component analysis may be used to determine those frequencies at which absorbance measurements are most informative. Other variations of the method involve eigen function analysis to determine a set of basic eigenspectra that characterize absorbance data within the wavelengths of interest for the chemicals of interest.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. A formation tester tool for analyzing a formation fluid in a formation surrounding a wellbore having a borehole fluid, the tester tool comprising:

(a) a reflectance crystal in contact with the formation fluid in the formation;

(b) a first optical channel for carrying monochromatic incident light having a wavelength from a source thereof to the reflectance crystal, said reflectance crystal having a surface angled at a critical angle;

(c) a second optical channel for carrying light reflected from within the reflectance crystal, said reflected light responsive to an absorbance of the formation fluid at said wavelength;

(d) an optical assembly for providing signals indicative of the energy of the incident light and the reflected light; and (e) a processor for determining said absorbance of the formation fluid at said wavelength from the signals indicative of the energy of the incident light and the reflected light.

2. The formation tester tool of claim 1 wherein the reflectance crystal is inserted into the formation on an optical probe.

3. The formation tester tool of claim 2 wherein the first and second optical channels are optic fibers carried by the optical probe.

4. The formation tester tool of claim 2 further comprising a drillbit for drilling a corehole in the formation, said corehole facilitating insertion of the optical probe into the formation.

5. The formation tester tool of claim 1 wherein the reflectance crystal is made of a material having a high refractive index.

6. The formation tester tool of claim 5 wherein the reflectance crystal is made of a material selected from the group consisting of (i) sapphire, (ii) cubic zirconia, and, (iii) diamond.

7. The formation tester tool of claim 1 wherein the source of the monochromatic light further comprises an acousto-optical tunable filter (AOTF) and a broad band light source on the optical assembly, said AOTF transmitting the incident monochromatic light to the first optical channel upon being provided with light from the broad band light source.

8. The formation tester tool of claim 7 wherein said wavelength is determined by a microwave signal to the AOTF from a radio frequency (RF) generator controlled by the processor.

9. The formation tester tool of claim 1 wherein said surface of the reflectance crystal is in contact with the formation fluid and a raypath of the incident light exceeds said critical angle at said surface.

10. The formation tester tool of claim 1 further comprising a pump for flowing formation fluid from the formation.

11. A system for analyzing a formation fluid in a formation surrounding a wellbore having a borehole fluid, the apparatus comprising:
   (a) a drill bit carried by a formation tester tool conveyed in the borehole on a wireline, said drill bit adapted for drilling a corehole into the formation;
   (b) an optical probe for insertion into the corehole, the optical probe including
      (i) a reflectance crystal at an end thereof, the reflectance crystal contacting the formation fluid,
      (ii) a first optical channel for carrying monochromatic incident light having a wavelength from a source thereof in the formation tester tool to the reflectance crystal, said reflectance crystal having a surface angled at a critical angle, and
      (iii) a second optical channel for carrying light reflected from within the reflectance crystal, said reflected light responsive to an absorbance of the formation fluid at said wavelength;
   (c) an optical assembly for providing signals indicative of the energy of the incident light and the reflected light; and
   (d) a processor for determining said absorbance of the formation fluid at said wavelength from the signals indicative of the energy of the incident light and the reflected light.

12. A method of analyzing a formation fluid in a formation surrounding a wellbore having a borehole fluid, the method comprising:
   (a) conveying a formation tester tool into the wellbore;
   (b) inserting an optical probe carrying a reflectance crystal on an end thereof into the formation to make contact with the formation fluid, said reflectance crystal having a surface angled at a critical angle;
   (c) conveying in a first optical channel on the probe a monochromatic incident light having a wavelength to the reflectance crystal and reflecting it from said surface within the reflectance crystal, as reflected light into a second optical channel on the probe;
   (d) providing signals indicative of the energy of the incident and reflected light in the first and second optical channels to a processor; and
   (e) processing said signals indicative of the energy of the incident and reflected light in the processor to determine an absorbance of the formation fluid at said wavelength.

13. The method of claim 12 further comprising using a drillbit on the formation tester tool for drilling a corehole into the formation for insertion therein of the optical probe.

14. The method of claim 12 wherein the step of reflecting the incident light in the crystal includes a total internal reflection.

15. The method of claim 12 further comprising generating the monochromatic incident light for conveying to the crystal by passing light from a broad band light source through an acousto-optical tunable filter (AOTF).

16. The method of claim 15 further comprising sending a microwave signal from a radio frequency (RF) generator under control of the processor to the AOTF, thereby determining the wavelength of the monochromatic incident light.

17. The method of claim 16 further comprising repeating said steps (a)–(e) of claim 12 at a plurality of wavelengths of the monochromatic light, thereby obtaining an absorbance spectrum for the formation fluid at said plurality of wavelengths.

18. The method of claim 17 further comprising determining a set of weights for representing said absorbance spectrum of the formation fluid as a weighted sum of absorbance spectra of known constituents.

19. The formation tester tool of claim 4 further comprising a pump for maintaining a fluid flow out of the formation for reducing the contamination by the borehole fluid of the formation fluid in contact with the probe.

20. The formation tester tool of claim 11 wherein the source of the monochromatic incident light further comprises an acousto-optical tunable filter (AOTF) and a broad band light source on the optical assembly, said AOTF transmitting the monochromatic incident light to the first optical channel upon being provided with light from the broad band light source.

21. The formation tester tool of claim 11 further comprising a pump for maintaining a fluid flow out of the formation thereby reducing the contamination by the borehole fluid of the formation fluid in contact with the probe.

22. The method of claim 12 further comprising maintaining the borehole fluid at a pressure less than a pressure of the formation fluid.

23. The method of claim 13 further comprising using a pump for maintaining a fluid flow out of the formation for reducing the contamination by the borehole fluid of the formation fluid in contact with the probe.

* * * * *